United States Patent [19]

Shephard

[11] Patent Number: 4,975,536
[45] Date of Patent: Dec. 4, 1990

[54] CONVERSION OF A DELTA16-STEROID TO A DELTA17(20)-20-SILYL ETHER

[75] Inventor: Kenneth P. Shephard, Kalamazoo, Mich.

[73] Assignee: The Upjohn Company, Kalamazoo, Mich.

[21] Appl. No.: 360,850

[22] Filed: Jun. 2, 1989

[51] Int. Cl.$^5$ ............................................. C07J 75/00
[52] U.S. Cl. ........................................ 540/3; 552/504; 552/505; 540/4
[58] Field of Search ................. 540/3, 4; 552/504, 505

[56] References Cited

U.S. PATENT DOCUMENTS 4,568,492 2/1986 Walker ..................... 260/239.55 R

OTHER PUBLICATIONS

T. Tsuda et al., Copper(I)-Catalysed Conjugate Reduction of α,β-Unsaturated Carbonyl Compounds by Lithium Aluminum Hydride, J. C. S. Chem. Comm., pp. 1013–1014 (1980).

T. Tsuda et al., Methylcopper(I)-Catalyzed Selective Conjugate Reduction of α,β-Unsaturated Carbonyl Compounds by Diisobutylaluminum Hydride in the Presence of Hexamethylphosphoric Triamide, J. Org. Chem., 51(No. 4): 537–540 (1986).

T. Tsuda et al., Stereoselective Synthesis of Angularly Methylated Trans Fused Hydrindanone by Conjugate Reduction, Syn. Comm., 16(6):639–643 (1986).

T. Tsuda et al., Alkylation and Silylation of the Aluminum Enolates Generated by Hydroalumination of α,β-Unsaturated Carbonyl Compounds, J. Org. Chem., 52(No. 3):439–443 (1987).

E. J. Corey and N. W. Boaz, Evidence for a Reversible d,π*-Complexation α,β-Cupration Sequence in the Conjugate Addition Reaction of Gilman Reagents with, -Enones, Tet. Lett., 26(No. 49):6015–6018 (1985).

E. J. Corey and N. W. Boaz, The Reactions of Combined Organocuprate-Chlorotrimethylsilane Reagents with Conjugated Carbonyl Compounds, Tet. Lett., 26(No. 49):6019–6022 (1985).

Y. Horiguchi et al., Me$_3$SiCl/HMPA Accelerated Conjugate Addition of Catalitic Copper Reagent. Stereoselective Synthesis of Enol Silyl Ether of Aldehyde, Tet. Lett., 27(No. 34):4025–4028 (1986).

E. Nakamura et al., Me$_3$SiCl Accelerated Conjugate Addition of Stoichiometric Organocopper Reagents, Tet. Lett., 27(No. 34): 4029–4032 (1986).

L. A. Paquette et al., Preparation and X-Ray Crystal Structure Analysis of a Stable Trimethylsilyloxy Epoxide, Tet. Lett., 28(No. 13):1363–1366 (1987).

C. Iwata et al., Oxidation of 2-Trimethylsilyloxy-1,3-Dienes with Triphenyl Phosphite Ozonide, Tet. Lett., 26(No. 27):3227–3230 (1985).

Primary Examiner—Mukund J. Shah
Assistant Examiner—E. C. Ward

[57] ABSTRACT

The present invention is a process for conversion of $\Delta^{16}$-steroids (I)

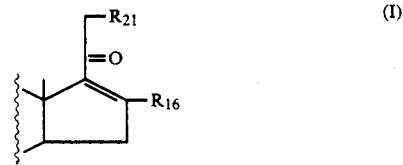

to the corresponding $\Delta^{17(20)}$-20-silyl ether (III)

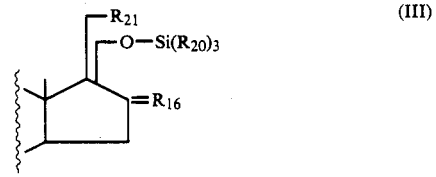

by reaction with (1) a preformed copper hydride or a metal hydride reducing agent in the presence of a copper species and (2) a silylating agent. The $\Delta^{17(20)}$-20-silyl ether (III) are useful intermediates in the preparation of steroids useful as pharmaceuticals.

21 Claims, No Drawings

CONVERSION OF A DELTA16-STEROID TO A DELTA17(20)-20-SILYL ETHER

BACKGROUND OF THE INVENTION

1. Field of the Invention

The present invention involves two processes for the transformation of a $\Delta^{16}$-steroid to a $\Delta^{17(20)}$-20-silyl ether which is a useful intermediate in the synthesis of corticoids.

2. Description of the Related Art

A copper iodide catalyzed conjugate reduction of an $\alpha,\beta$-unsaturated ketone (cyclohex-2-enone) by lithium aluminum hydride (LAH) in hexamethylphosphoric triamide (HMPA)/THF is reported in J. Chem. Soc. Chem. Comm., 1013 (1980). Similarly, J. Org. Chem., 51, 537 (1986) reports conjugate reduction of a steroidal $\alpha,\beta$-unsaturated ketone (progesterone) with diisobutylaluminum hydride (DIBAH), catalytic amount of methylcopper(I) and HMPA to give 84% of the reduced A-ring and 6% of the corresponding 20-hydroxy-$\Delta^4$-3-ketone When this process was applied to the $\Delta^{16}$-steroids (I) of the present invention, the steroid A-ring was not reduced, but there was selective reduction of the $\Delta^{16}$-20-keto functionality at the D-ring. The conjugate reduction process of the present invention is operable with both $\Delta^4$-3-keto and $\Delta^{1,4}$-3-keto steroids Syn. Comm. 16, 639 (1986) and J. Org. Chem., 52 439 (1987) both report the reaction of an $\alpha,\beta$-unsaturated ketone with DIBAH, a catalytic amount of methylcopper(I) and HMPA. The latter reference reports when the aluminum enolate produced was silylated the product produced was the reduced silyl enol ether, stating "The high efficiency of the conjugate reduction indicates the quantitative formation of the aluminum enolate by the hydroalumination of $\alpha,\beta$-unsaturated carbonyl compounds with DIBAH-HMPA." When this process was performed on the $\Delta^{16}$-steroids (I) of the present invention, no evidence of any silyl enol ether was observed.

Tet. Lett. 26, 6015 (1985), ibid 26, 6019 (1985), ibid 27, 4025 (1986) and ibid 27, 4029 (1986) all describe the reaction of conjugated carbonyl compounds with organocopper reagents in the presence of trimethylsilyl chloride to give the expected silyl enol ether. The silylating agent not only accelerated the reactions but also gave higher yields. When the copper catalyzed conjugate reduction of the $\Delta^{16}$-steroids (I) of the present invention was performed in the presence of trimethylsilyl chloride only a small amount of the silyl enol ether (III) was formed.

U.S. Pat. No. 4,568,492 discloses the reaction of $\Delta^{16}$-steroids with trimethylsilyl chloride catalyzed by $(\phi P)_3RhCl$ to give the $\Delta^{17(20)}$-20-silyl enol ether, but we have found that the process is not operable with a $\Delta^{1,4}$-3-keto functionality in the steroid A-ring. Tet. Lett. 28, 1363 (1987) describes the peracid oxidation of a non-steroidal enol ether to give the corresponding epoxy-silyl ether and the subsequent isolation of a non-steroidal epoxy-silyl ether. In order to isolate the epoxy-silyl ether very mild reaction conditions were used and sodium bicarbonate was added to the reaction mixture to neutralize the acid product of the peracid reactant. Tet. Lett., 26, 3227 (1985) reports a steroidal epoxy-silyl ether where the epoxy-silyl ether functionality was in the steroid A-ring. This compound was not isolatable. The present invention does not require addition of a base such as sodium bicarbonate in order to isolate the $17\alpha,20\alpha$-epoxy-20-silyl ether (IV).

SUMMARY OF INVENTION

Disclosed is a process for the production of a metal enolate of formula (II) where:

$R_{16}$ is $\alpha$-H:$\beta$-$R_{16\text{-}2}$ where $R_{16\text{-}2}$ is —H or —CH$_3$;
$R_{21}$ is —H, —O—$R_{21\text{-}1}$ where $R_{21\text{-}1}$ is —H, $C_1$-$C_4$ alkyl, —CH$_2$—O—CH$_3$, —CHR$_{21\text{-}2}$—O—$R_{21\text{-}3}$ where $R_{21\text{-}2}$ is $C_1$-$C_4$ alkyl and $R_{21\text{-}3}$ is $C_1$-$C_4$ alkyl, —CH$_2$—O—CH$_2$CH$_2$—O—$R_{21\text{-}4}$ where $R_{21\text{-}4}$ is $C_1$-$C_4$ alkyl, THP, —CO—$R_{21\text{-}5}$ where $R_{21\text{-}5}$ is $C_1$-$C_4$ or —$\phi$, —Si($R_{21\text{-}6}$)$_3$ where the $R_{21\text{-}6}$'s are the same or different and are selected from the group consisting of $C_1$-$C_4$ alkyl and —$\phi$;
$M_{20}$ is copper or a metal ion derived from the metal hydride reducing agent, which comprises contacting a $\Delta^{16}$-steroid of formula (I) where $R_{16}$ is —H or —CH$_3$ and $R_{21}$ is as defined above with a member selected from the group consisting of a preformed copper hydride or a metal hydride reducing agent in the presence of a copper species.

Also disclosed is a process for the production of a silyl ether of formula (III) where
$R_{16}$ is $\alpha$—H:$\beta$—$R_{16\text{-}2}$ where $R_{16\text{-}2}$ is —H or —CH$_3$;
$R_{20}$'s are the same or different and are $C_1$-$C_7$ alkyl or —$\phi$;
$R_{21}$ is —H, —O—$R_{21\text{-}1}$ where $R_{21\text{-}1}$ is —H, $C_1$-$C_4$ alkyl, —CH$_2$—O—CH$_3$, —CHR$_{21\text{-}2}$—O—$R_{21\text{-}3}$ where $R_{21\text{-}2}$ is $C_1$-$C_4$ alkyl and $R_{21\text{-}3}$ is $C_1$-$C_4$ alkyl, —CH$_2$—O—CH$_2$CH$_2$—O—$R_{21\text{-}4}$ where $R_{21\text{-}4}$ is $C_1$-$C_4$ alkyl, THP, —CO—$R_{21\text{-}5}$ where $R_{21\text{-}5}$ is $C_1$-$C_4$ or —$\phi$, —Si($R_{21\text{-}6}$)$_3$ where the $R_{21\text{-}6}$'s are the same or different and are selected from the group consisting of $C_1$-$C_4$ alkyl and —$\phi$; which comprises contacting a metal enolate of formula (II) where $M_{20}$ is a copper, aluminum or boron cation, and $R_{16}$ and $R_{21}$ are as defined above, with a silylating agent.

Further disclosed is a process for the production of a silyl ether of formula (III) where $R_{16}$ is $\alpha$—H:$\beta$—$R_{16\text{-}2}$ where $R_{16\text{-}2}$ is —H or —CH$_3$;
$R_{20}$'s are the same or different and are $C_1$-$C_7$ alkyl or —$\phi$
$R_{21}$ is —H, —O—$R_{21\text{-}1}$ where $R_{21\text{-}1}$ is —H, $C_1$-$C_4$ alkyl, —CH$_2$—O—CH$_3$, —CHR$_{21\text{-}2}$—O—$R_{21\text{-}3}$ where $R_{21\text{-}2}$ is $C_1$-$C_4$ alkyl and $R_{21\text{-}3}$ is $C_1$-$C_4$ alkyl, —CH$_2$—O—CH$_2$CH$_2$—O—$R_{21\text{-}4}$ where $R_{21\text{-}4}$ is $C_1$-$C_4$ alkyl, THP, —CO—$R_{21\text{-}5}$ where $R_{21\text{-}5}$ is $C_1$-$C_4$ or —$\phi$, —Si($R_{21\text{-}6}$)$_3$ where the $R_{21\text{-}6}$'s are the same or different and are selected from the group consisting $C_1$-$C_4$ alkyl and —$\phi$; which comprises contacting a $\Delta^{16}$-steroid of formula (I) where $R_{16}$ is —H or —CH$_3$ and $R_{21}$ is as defined above with a member selected from the group consisting of a preformed copper hydride or a metal hydride reducing agent in the presence of a copper species, in the presence of a silylating agent.

Disclosed is a steroidal—$17\alpha,20\alpha$-epoxide-20-silyl ether of formula (IVA) where (A-I) $R_6$ is $\alpha$—$R_{6\text{-}1}$:$\beta$—$R_{6\text{-}2}$, $R_{10}$ is $\alpha$—$R_{10\text{-}1}$:$\beta$—$R_{10\text{-}2}$ and $R_7$ is $\alpha$—H:$\beta$—H where one of $R_{6\text{-}1}$ and $R_{6\text{-}2}$ is —H and the other is —H, —F or —CH$_3$, $R_{10\text{-}2}$ is —CH$_3$, $R_{10\text{-}1}$ and $R_5$ taken together are —CH$_2$—CH$_2$—CO—CH= or —CH=CH—CO—CH=;

(A-II) $R_6$ is $R_{6\text{-}3}$:$R_{6\text{-}4}$, $R_7$ is $R_{7\text{-}3}$:$R_{7\text{-}4}$, $R_{10}$ is $\alpha$—$R_{10\text{-}3}$:$\beta$—$R_{10\text{-}4}$ where one of $R_{6\text{-}3}$ and $R_{6\text{-}4}$ is —H and the other taken together with one of $R_{7\text{-}3}$ and $R_{7\text{-}4}$ forms a second bond between $C_6$ and $C_7$, and the other of $R_{7\text{-}3}$ and $R_{7\text{-}4}$ is —H, $R_{10\text{-}4}$ is —CH$_3$, $R_{10\text{-}3}$ and $R_5$ taken together are $-CH_2-CH_2-CO-CH=$ or $-CH=CH-CO-CH=$;

(C-I) $R_{11}$ is $R_{11-1}$:$R_{11-2}$, where one of $R_{11-1}$ and $R_{11-2}$ is taken together with $R_9$ to form a second bond between $C_9$ and $C_{11}$ and the other of $R_{11-1}$ and $R_{11-2}$ is $-H$;

(C-II) $R_{11}$ is $\alpha-H$:$\beta-O-$ where $\beta-O-$ is taken together with $R_9$ to form an epoxide between $C_9$ and $C_{11}$ in the $\beta$-configuration:

(C-III) $\alpha-R_9$ is $-H$, $-Br$, $-Cl$, $-F$ and $R_{11}$ is $=O$ or $\alpha-R_{11-3}$: $R_{11-4}$ where one of $R_{11-3}$ and $R_{11-4}$ is $-H$ and the other of $R_{11-3}$ and $R_{11-4}$ is $-H$ or $-OH$;

(C-IV) $R_9$ is $-OH$ and $R_{11}$ is $\alpha-H$:$\beta-H$;

$R_{16}$ is $\alpha-H$:$\beta-R_{16-2}$ where $R_{16-2}$ is $-H$ or $-CH_3$;

$R_{20}$'s are the same or different and are $C_1-C_7$ alkyl or $R_{21}$ is $-H$, $-O-R_{21-1}$ where $R_{21-1}$ is $-H$, $C_1-C_4$ alkyl, $-CH_2-O-CH_3$, $-CHR_{21-2}-O-R_{21-3}$ where $R_{21-2}$ is $C_1-C_4$ alkyl and $R_{21-3}$ is $C_1-C_4$ alkyl, $-CH_2-O-CH_2CH_2-O-R_{21-4}$ where $R_{21-4}$ is $C_1-C_4$ alkyl, THP, $-CO-R_{21-5}$ where $R_{21-5}$ is $C_1-C_4$ or $-\phi$, $-Si(R_{21-6})_3$ where the $R_{21-6}$'s are the same or different and are selected from the group consisting of $C_1-C_4$ alkyl and

DETAILED DESCRIPTION OF THE INVENTION

The $\Delta^{16}$-steroids (I) are known to those skilled in the art or can readily be prepared from known starting materials, see for example, U.S. Pat. Nos. 2,864,834 ($\Delta^{16}$-steroids) and 3,461,144 (16-methyl-$\Delta^{16}$-steroids).

The process of the present invention will differ depending on whether or not it is desired to obtain a solution of the 20-metal enolate (II) or proceed with a silylating agent present which gives directly the $\Delta^{17(20)}$-silyl ether (III). It is preferred to convert the $\Delta^{16}$-steroid (I) directly to the $\Delta^{17(20)}$-silyl ether (III).

The $\Delta^{16}$-steroid (I) is contacted with a member selected from the group consisting of a preformed copper hydride or a metal hydride reducing agent in the presence of a copper species in order to produce the 20-metal enolate (II). Metal is copper or a metal ion derived from the metal hydride reducing agent. It is understood in the art that $M_{20}$ is a copper, aluminum, substituted aluminum or boron cation which may contain other fragments besides the particular metal. Preformed copper hydride includes $[(\phi_3P)CuH]_6$, $(CuH)_x$ where x is from 1 thru 6, $LiCuH_2$, $LiCu_2H_3$, $Li_2Cu_3H_5$, $Li_2CuH_3$, $Li_3CuH_4$, $Li_4CuH_5$, $LiCuH_6$, $Li_5CuH_6$, $CH_3CH_2CH_2-C\equiv CuHLi$, t-butyl-O-CuHLi and $\phi SCuHLi$. With $(CuX)_x$ it is understood that the copper is an aglomerate complex, with "x" believed to be 1-6. The preformed copper, for example $[(\phi_3P)Cu-H]_6$, can be prepared as described in Tet. Lett. 29, 3749 (1988) or J.A.C.S. 110, 291 (1988) and then added to the reaction mixture. Alternatively the copper hydride can be prepared in situ by reaction of a metal hydride reducing agent and a copper species. Suitable metal hydride reducing agents include (A) $(X_2)(X_3)Al-H$ where $X_2$ and $X_3$ are the same or different and are $C_1-C_6$ alkyl;

(B) $[Cation]^+[(X_4)_3Aluminum-H]^-$ where Cation is sodium, potassium or lithium, $X_4$ are the same or different and are $-H$ or $-O-X_{4-1}$ where $X_{4-1}$ is $C_1-C_6$ alkyl;

(C) $(Metal)(X_5)_3B-H$ where metal is sodium, potassium or lithium and $X_5$ is $-H$, $C_1-C_6$ alkyl, $---O-X_{5-1}$ where $X_{5-1}$ is $C_1-C_6$ alkyl, $-CO-X_{5-1}$ where $X_{5-1}$ is as defined above.

Preferred are DIBAH, LAH and $(Metal)(X_5)B-H$ where metal is sodium or potassium and $X_5$ is $-CH(CH_3)-CH(CH_3)_2$ or $CH(CH_3)-CH_2-CH_3$; more preferred is DIBAH or LAH. Suitable copper species include any soluble copper (I) or (II) compound, or solubilized form of the copper species. Preferred are (1) $Cu(I)X_6$ where $X_6$ is $-CH_3$, $-Cl$, $-Br$, $-I$, $-CN$, acetate, propionate;

(2) $Cu(II)(X_7)_n$ where $X_7$ is $-CH_3$, $-Cl$, $-Br$, $-I$, $-CN$, sulfate, acetate, propionate and (3) dilithium tetrachlorocuprate $(Li_2CuCl_4)$. More preferred are copper-(II)propionate and acetate, copper(I)iodide, chloride, bromide and cyanide; most preferred are copper(II)propionate and acetate. When the copper hydride is produced using DIBAH as the hydride source, the enolate has as its cation the diisobutylaluminum moiety, as defined above. When one equivalent of $[(\phi_3P)CuH]_6$ is used, the copper enolate is obtained.

The active species is the copper hydride. If used as such, one equivalent is required. Less than one equivalent (a catalytic amount) can be used if a reducing agent is present to regenerate the active species. For example, if $[(\phi_3P)Cu-H]_6$ is used as the copper hydride (active species) one equivalent is operable. Catalytic amounts can be used if hydrogen, or other appropriate hydride source, is also used to regenerate the active species. More than one equivalent is operable, just not needed and wasteful.

The $\Delta^{16}$-steroid (I) and a preformed copper hydride or a metal hydride reducing agent in the presence of a copper species are contacted in an anhydrous aprotic solvent, such as an ether or nonhalogenated aromatic hydrocarbon. Preferred solvents include tetrahydrofuran, dioxane, ether, diglyme, toluene and HMPA; more preferred is tetrahydrofuran. The reaction is operable in a temperature range of about $-100°$ to about $50°$; preferably about $-30°$ to about $-60°$. The order of contacting the reactants is not critical.

While not necessary, it is preferred the contacting take place in the presence of a ligand. Suitable ligands include HMPA, DMI, DMPU, TMU, NMP, TES, DMAP, TMEDA and $(X_{20})_3P$ where $X_{20}$ is $C_1-C_8$ alkyl or $-\phi$. Preferred ligands are HMPA, DMI, DMPU, TMU and NMP.

Preferably the metal enolate (II) is not isolated but carried on in situ to give the $\Delta^{17(20)}$-silyl ether (III).

The metal enolate (II) is converted to the $\Delta^{17(20)}$-silyl ether (III) by contacting with a silylating agent. Operable silylating agents include (1) $X_1-Si-(R_{20})_3$ where $X_1$ is $-Cl$, $-Br$, $-I$ and where $R_{20}$ is as defined in claim 8, in the presence of an amine catalyst; (2) a silylated imidazole of formula (IM-1) where $X_8$, $X_9$ and $X_{10}$ are the same or different and are $-H$ or $C_1-C_3$ alkyl, (3) a 1-silylated 1,2,4-triazole of the formula $*NSi(R_{20})_3-N=CX_{17}-N=CX_{18}*$ where $X_{17}$ and $X_{18}$ are the same or different and are $-H$ or $C_1-C_3$ alkyl, and the atoms marked with an asterisk are bonded to each other resulting in the formation of a ring, (4) a 1-silylated tetrazole of the formula $*N(R_{20})_3-N=N-N=CX_{19}*$ where $X_{19}$ is $-H$ or $C_1-C_3$ alkyl and where the atoms marked with an asterisk are bonded to each other resulting in the formation of a ring, (5) a 3-silylated benzimidazole optionally substituted with 1-5 $C_1-C_3$ alkyl in the 2-, 4-, 5-, 6- and 7-positions. When the silylating agent is a silyl halide then the contacting must be in the presence of an amine catalyst. It is preferred the silylating agent be selected from the group consisting of trimethylsilylhalide, diphenylmethylsilylhalide, diphenylmethylsilylimidazole or trimethylsilylimidazole, more preferably trimethylsilyl chloride or trimethylsilylimidazole. It is preferred that $R_{20}$ is —$CH_3$ or —$\phi$; more preferred that $R_{20}$ is —$CH_3$. The contacting of the metal enolate (II) with the silylating agent is performed in the presence of an amine catalyst when the silylating agent is a silyl halide. Suitable amine catalysts include pyridine, triazene, tetrazene, an imidazole of formula (IM-2) where $X_{11}$, $X_{12}$ and $X_{13}$ are the same or different and are —H or $C_1$-$C_3$ alkyl, a 1,2,4-triazole of the formula *NH—N=$CX_{14}$—N=$CX_{15}$* where $X_{14}$ and $X_{15}$ are the same or different and are —H or $C_1$-$C_3$ alkyl and the atoms marked with an asterisk are bonded to each other resulting in the formation of a ring, a tetrazole of the formula *NH—N=N—N=$CX_{16}$* where $X_{16}$ is —H or $C_1$-$C_3$ alkyl and where the atoms marked with an asterisk are bonded to each other resulting in the formation of a ring, benzimidazole optionally substituted with 1-5 $C_1$-$C_3$ alkyl in the 2-, 4-, 5-, 6- and 7-positions. Preferred amine catalysts are imidazole, dimethylimidazole, triazole, tetrazole and benzimidazole; more preferred is imidazole. It is preferable to add additional amine catalyst during the reaction to ensure completion of the reaction.

The 20-metal enolate (II) and silylating agent are contacted in the same solvent that is operable for the production of the 20-metal enolate (II). The reaction is operable in a temperature range of about −80° to about 80°; preferably about −60° to about 40°; more preferably about −60° to about 25°.

It is preferable to perform the process of the invention, the transformation of the $\Delta^{16}$-steroids (I) to the corresponding $\Delta^{17(20)}$-20-silyl ethers (III) in one step by contacting the $\Delta^{16}$-steroid (I) (1) with a preformed copper hydride or a metal hydride reducing agent in the presence of a copper species and (2) in the presence of a silylating agent. It is preferred that the contacting take place in the presence of a ligand. The preferred reagents are as described above.

The $\Delta^{17(20)}$-20-silyl ethers (III) are transformed by known methods (peracid) to the corresponding 17α,20α-epoxide-20-silyl ethers (IV). The 17α,20α-epoxide-20-silyl ethers (IV) can be isolated if desired by addition of the reaction mixture to a dilute solution of aqueous acetic acid. The product is then extracted with an appropriate organic solvent.

The 17α,20α-epoxide-20-silyl ethers (IV) are transformed by acid or base to the corresponding corticoids (V) which have a known utility in the pharmaceutical area as anti-inflammatory agents.

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—C(=$Z_1$)H. Groups $R_i$ and $R_j$ would represent monovalent variable substituents if attached to the formula $CH_3$—$CH_2$—C($R_i$)($R_j$)$H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=C($CH_3$)—CF=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In formulas depicting such compounds, a substituent ($X_1$) which is "below" another substituent ($X_2$) will be identified as being in the alpha (α) configuration and is identified by a broken, dashed or dotted line attachment to the carbon atom, i.e., by the symbol "- - -" or "...". The corresponding substituent attached "above" ($X_2$) the other ($X_1$) is identified as being in the beta (β) configuration and is indicated by an unbroken line attachment to the carbon atom.

When a variable substituent is bivalent, the valences may be taken together or separately or both in the definition of the variable. For example, a variable $R_i$ attached to a carbon atom as $-C(=R_i)-$ might be bivalent and be defined as oxo or keto (thus forming a carbonyl group (—CO—) or as two separately attached monovalent variable substituents $\alpha-R_{i\text{-}j}$ and $\beta-R_{i\text{-}k}$. When a bivalent variable, $R_i$, is defined to consist of two monovalent variable substituents, the convention used to define the bivalent variable is of the form "$\alpha-R_{i\text{-}j}:\beta-R_{i\text{-}k}$" or some variant thereof. In such a case both $\alpha-R_{i\text{-}j}$ and $\beta-R_{i\text{-}k}$ are attached to the carbon atom to give $-C(\alpha-R_{i\text{-}j})(\beta-R_{i\text{-}k})-$. For example, when the bivalent variable $R_6$, $-C(=R_6)-$ is defined to consist of two monovalent variable substituents, two monovalent variable substituents are $\alpha-R_{6\text{-}1}:\beta-R_{6\text{-}2}, \ldots \alpha-R_{6\text{-}9}:\beta-R_{6\text{-}10}$, etc, giving $-C(\alpha-R_{6\text{-}1})(\beta-R_{6\text{-}2})-, \ldots -C(\alpha-R_{6\text{-}9})(\beta-R_{6\text{-}10})-$, etc. Likewise, for the bivalent variable $R_{11}$, $-C(=R_{11})-$, two monovalent variable substituents are $\alpha-R_{11\text{-}1}:\beta-R_{11\text{-}2}$. For a ring substituent for which separate $\alpha$ and $\beta$ orientations do not exist (e.g. due to the presence of a carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula $-C_1(R_i)H-C_2(R_j)H-$ ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form $-CH_2-CH_2-O-CO-$ . . . " means a lactone in which the carbonyl is bonded to $C_2$. However, when designated " . . . $R_j$ and $R_i$ are taken together to form $-CH_2-CH_2-O-CO-$ the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3-(CH_2)_n-O-CO-$ where n is zero, one or 2. By the second method the carbon atom content of only each portion of the definition is indicated separately by enclosing the "$C_i$—$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. DEFINITIONS

All temperatures are in degrees Centigrade.
TLC refers to thin layer chromatography.
THF refers to tetrahydrofuran.
DIBAH refers to diisobutylaluminum hydride.
LAH refers to lithium aluminum hydride.
HMPA refers to hexamethylphosphoric triamide.
DMI refers to 1,3-dimethyl-2-imidazolidinone.
DMPU refers to N,N'-dimethylpropyleneurea.
TMU refers to tetramethylurea.
NMP refers to N-methylpyrrolidinone.
TES refers to tetraethylsulfone.
DMAP refers to dimethylaminopyridine.
TMEDA refers to tetramethylethylenediamine.
Ether refers to diethyl ether.
Saline refers to an aqueous saturated sodium chloride solution.
$\phi$ refers to phenyl ($C_6H_5$).

When solvent pairs are used, the ratios of solvents used are volume/volume (v/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

20,21-Dihydroxy-16α-methylpregna-1,4,9(11),17(20)-tetraen-3-one 21-acetate 20-trimethylsilyl ether Under an inert atmosphere, copper(II) propionate (2.191 g) is dissolved in anhydrous THF (132 ml) and 1,3-dimethyl-2-imidazolidinone (48.0 ml). The mixture is cooled to < −30° and methylmagnesium chloride (2.07M, 12.0 ml) is added slowly to maintain the low temperature. The resulting mixture is transferred rapidly into a slurry of 21-hydroxyypregna-1,4,9(11),16-tetraene-3,20-dione 21-acetate (U.S. Pat. No. 4,031,080 Example 1, 76.66 g) anhydrous THF (832 ml) and stirred at < −50°. Chlorotrimethylsilane (34.5 ml) is added to the chilled slurry. This mixture is aged for 10 minutes and then methylmagnesium chloride (2.07M, 101 ml) is added over a period of 75 min. An extra 6.0 ml of the Grignard reagent is added during the next 50 min to consume the starting material. The reaction mixture is quenched by adding toluene (1.24 l) and aqueous acetic acid (5%, 1.24 l). The two phases are separated after 45 min of vigorous mixing at 5°. The aqueous phase is extracted with toluene (200 ml) and the two toluene solutions are combined. This net solution is washed with aqueous acetic acid (5%, 2×400 ml) and dried with magnesium sulfate. The drying agent is removed by filtration and the filtrate is concentrated under reduced pressure to give the title compound.

PREPARATION 2
17α-Bromo-21-hydroxy-16α-methylpregna-1,4,9(11)-triene-3,20-dione 21-acetate A slurry, prepared from N-bromosuccinimide (40.96 g), acetone (225 ml) and water (37.7 ml) is cooled to <−40°. A mixture of 20,21-dihydroxy-16α-methylpregna-1,4,9(11),17(20)-tetraen-3-one 21-acetate 20-trimethylsilyl ether (PREPARATION 1, 99.56 g) and acetone (350 ml) is added slowly while keeping the temperature less than −35°. The silyl ether (III) is consumed within one hour and n-butyl vinyl ether (5.41 ml) is added to quench any access brominating agent. The quenching reaction proceeds for 20 min at a temperature of <−30° and is then warmed to 5°. When this temperature is reached, water (400 ml) and toluene (200 ml) are added. The two phases are separated after adequate mixing. The aqueous phase is extracted with toluene (100 ml). The toluene solutions are combined and washed with water (200 ml). Magnesium sulfate is used to dry the solution, which is concentrated under reduced pressure. The mixture is filtered to give the title compound.

PREPARATION 3
21-Hydroxy-16-methylpregna-1,4,9(11),16-tetraene-3,20-dione 21-acetate (I)

Lithium carbonate (30.92 g) and lithium bromide (18.17 g) is added to a solution of 17α-bromo-21-hydroxy-16α-methylpregna-1,4,9(11)-triene3,20-dione (PREPARATION 2, 98.43 g) in DMF. The solids are rinsed into the solution with DMF sufficient to bring the total amount to 350 ml. The reaction is warmed to 96° over a 3 hr and forty minute period. It is then transferred to a dropping funnel with 15 ml of DMF and added over a 40 min period to 3.4 l of vigorously stirred half-saturated saline. The funnel is rinsed with DMF (15 ml) and the knockout slurry is cooled to <10°. After 30 min, the product is collected by filtration and washed thoroughly with water (3×250 ml). The moist solids are dried with nitrogen flow to give the title compound.

EXAMPLE 1
17Z- and 17E-isomers of 6α-fluoro-20,21-dihydroxy-pregna-1,4,9(11),17(20)-tetraene-3-one 21-acetate 20-trimethylsilyl ether (III)

A solution of copper propionate (0.545 g) in THF (110 ml) is added to a precooled −50° slurry of 6α-fluoro-21-hydroxypregna-1,4,9(11),16-tetraene-3,20-dione 21-acetate (I, U.S. Pat. No. 3,210,341 Example 1, 20.00 g) in THF (150 ml) containing dimethylimidazolidinone (9.10 ml) and N-trimethylsilylimidazole (15.3 ml) under a nitrogen atmosphere over a 5 min period. The suspension is stirred for 5 min, then a solution of DIBAH (25%, 55.27 ml) in toluene is added slowly dropwise over a 40.50 min period. The reaction is monitored by TLC [the TLC sample is obtained by diluting 0.5 ml of the reaction mixture with tetrahydrofuran (0.5 ml) and eluting with tetrahydrofuran/heptane (40/60), title compound (III) Rf=0.64] during the addition and when the reduction is complete the DIBAH addition is discontinued.

Imidazole (1.77 g) is added and the reaction is allowed to warm to 20°–25° C. After reaching 20°–25° the reaction is checked for complete silylation by TLC.

When the silylation is complete the reaction is quenched by adding it to a mixture of aqueous acetic acid (1.5%, 1250 ml) and toluene (250 ml) at 0°. The mixture is stirred for 5–10 minutes, then the layers are separated. The aqueous layer is extracted with toluene (2×200 ml) and the combined organic extracts are washed with H$_2$O (2×300 ml) and then with saline (300 ml). The organic layer is dried over magnesium sulfate and filtered. The toluene is removed under reduced pressure to give the title compound in a total volume of 220 ml. The title compound is used in the oxidation reaction (EXAMPLE 2) without further purification.

EXAMPLE 2
17Z- and 17E-isomers of 6α-fluoro-17α,21-dihydroxy-pregna-1,4,9(11)-triene-3,20-dione 21-acetate (V)

Sodium acetate (0.384 g) is added to a solution of 6α-fluoro-20,21-dihydroxypregna-1,4,9(11),17(20)-tetraene-3-one 20-trimethyl silyl ester 21 acetate (III, EXAMPLE 1, 23.86 g) in toluene (220 ml total volume) under nitrogen. The reaction is cooled to 0° and peracetic acid (15.1 ml) is added dropwise over 5 minutes. A 5° exotherm is observed. The reaction is allowed to stir at 0° for 30–45 min, then it is checked by TLC [ethyl acetate/heptane (1/1), the epoxide (IV) has an R$_f$ of just a little less than the silyl ether (III)].

When the reaction is complete, to check for peroxides, sodium bisulfite (6.60 g) in water (84 ml) is added over 5 min and the temperature rises to 30° to 40°. The product precipitates as a dense solid which stays in the aqueous layer when stirring is stopped. Heptane (180 ml) is added over 5.10 min and the slurry is cooled in an ice bath for 30 minutes. The product is isolated by filtration and washed thoroughly with water (5×100 ml).

EXAMPLE 3
17Z- and 17E-isomers of 20,21-dihydroxy-16-methylpregna-1,4,9(11),17(20)-tetraen-3-one 21-acetate 20-trimethylsilyl ether (III)

Anhydrous THF (106 ml) and HMPA (12.2 ml) are added to 21-hydroxy-16-methylpregna-1,4,9(11),16-tetraene-3,20-dione 21-acetate (I, PREPARATION 3, 5.33 g) and cuprous cyanide (500 g) contained under an inert atmosphere. This mixture is stirred for 10 min at 23° and then it is cooled to <−40° before trimethylsilylimidazole (4.2 ml) and LAH (95%, 0.211 g) are added to it. The reaction is held at a temperature less than or equal to −40° for 3 hr and periodic additions of fresh trimethylsilylimidazole (1.63 ml) and LAH (0.145 g) are required to complete the reduction. The reaction is then treated with acetone (3.50 ml) and imidazole (0.482 g). It is warmed to 23° and aged at this temperature for 1 hr before it is poured into aqueous acetic acid (2%, 420 ml) and hexane (250 ml) and stirred vigorously at 0°. This mixture is filtered through a celite pad, which is washed with aqueous acetic acid (2%, 50 ml) and hexane (200 ml). The two phases of the filtrate are separated. The aqueous phase is extracted with hexane (2×60 ml). The organic phases are combined and then washed with water (3×) and saline (56 ml). Residual water is removed with sodium sulfate. The drying agent is removed by filtration and the filtrate is concentrated under reduced pressure at 38° to give the title compounds as an oil.

EXAMPLE 4
17Z- and 17E-isomers of 20,21-dihydroxy-16β-methylpregna-1,4,9(11),17(20)-tetraen-3-one 21-acetate 20-trimethylsilyl ether (III)

DIBAH (1.50M, 16.0 ml) in toluene is added to a mixture of cupric propionate (0.314 g), anhydrous THF (10.0 ml) and HMPA (5.20 ml) stirred at $<-60°$ under an inert atmosphere. The mixture is added rapidly to a solution of 21-hydroxy 16-methylpregna-3,20-dione-1,4,9,16-tetraene 21-acetate (I, PREPARATION 3, 5.71 g), THF (75.0 ml) and trimethylsilylimidazole (6.60 ml) and stirred at $<-50°$. The reaction proceeds at this temperature for 4.5 hr, over which time five portions of fresh copper hydride, each prepared from cupric propionate (0.157 g), THF (5.0 ml), HMPA (0.91 ml) and DIBAH (1.5M, 3.00 ml), are added. Imidazole (0.532 g) is added, the reaction is warmed to 20° and then it is stirred for 14 hr. The mixture is poured into hexane (300 ml) and aqueous acetic acid (2%, 300 ml) and stirred vigorously at $<10°$. An emulsion results which is filtered through a bed of celite. The two phases in the filtrate are separated and the aqueous phase is extracted with hexane (100 ml). The organic extracts are combined and then washed with water (4×100 ml) and saline (50 ml). The residual water is removed with sodium sulfate. The dried hexane solution is concentrated under reduced pressure to give the title compounds as an oil. LC shows the oil to be a mixture (46.6/1) of 17Z-/17E-.

EXAMPLE 5
17Z- and 17E-isomers of 17α,21-dihydroxy-16β-methylpregna-1,4,9(11)-triene-3,20-dione 21-acetate (V)

A solution, prepared from crude 21-hydroxy-16β-methylpregna-1,4,9(11),17(20)-tetraen-3-one 21-acetate 20-trimethylsilyl ether (III, EXAMPLE 4, 3.906 g) and toluene (39.0 ml), is cooled to $<5°$ and sodium acetate (0.072 g) is added. Peracetic acid (5.57M, 2.31 ml) is added slowly. The reaction is kept at a temperature $<520$ for 3.5 hr. A solution of sodium sulfate (2.34 g) in water (7.50 ml) is then added. The quenched reaction is stirred for 19 hr at 23°. Then hydrochloric acid (37%, 3.75 ml) is added portionwise over 7 hr. Heptane (25 ml) is then added and the mixture is cooled to 2°. The product is isolated by filtration of the acidic mixture. It is washed with water (3×12 ml) and heptane (2×10 ml). The product is dried with a nitrogen gas flow to give the title compound. The toluene layer of the filtrate is treated with acetone (10 ml) and then washed with water (2×10), aqueous sodium bicarbonate (5%, 15 ml) and additional water (15 ml). The solution is dried with magnesium sulfate and then concentrated at 50° under reduced pressure to give a second crop of the title compound.

EXAMPLE 6
17Z- and 17E-isomers of 9β,11β-epoxy-20,21-dihydroxypregna-1,4,17(20)-trien-3-one 21-acetate 20-trimethylsilyloxy ether (III)

A solution of copper propionate (0.137 g) in tetrahydrofuran (30 ml) under a nitrogen atmosphere is cooled in a dry ice/acetone bath to $-50°$. HMPA (3.64 ml) followed by a solution of DIBAH in toluene (25% wt, 13.3 ml) is added to the copper solution over a 5.10 min keeping the temperature near $-50°$. The solution turns dark green then lightens to brown during the addition. This brown solution is allowed to stir 3.5 min., then it is added via a cannula to a $-50°$ slurry of 9β,11β-epoxy-21-hydroxyprena-1,4,16-triene-3,20-dione 21-acetate (I, 5.000 g) in tetrahydrofuran (38 ml) containing N-trimethylsilylimidazole (6.71 ml) over a 12 min period. The $\Delta^{16}$-steroid starting material (I) requires one hr to go into solution. The solution is allowed to stir after complete addition and checked by TLC [the TLC sample is obtained by diluting 0.5 ml of the reaction mixture with tetrahydrofuran (0.5 ml) and eluting with tetrahydrofuran/heptane (40/60), title compound (III) Rf =0.64].

When the reduction is complete, imidazole (0.445 g) is added and the reaction is allowed to warm to 20°–25° at which time the reaction is checked for complete silylation by TLC, as described above.

When the silylation is complete, the reaction is quenched by adding it to a 0° mixture of aqueous acetic acid (1.5%, 500 ml) and toluene (125 ml). The mixture is allowed to stir 5.10 min, then the layers are separated. The aqueous layer is extracted with toluene (2×100 ml) and the combined organic extracts are washed with water (2×1200 ml) and then with saline (100 ml). The organic layer is dried over magnesium sulfate, filtrated and concentrated under reduced pressure to a total volume of 35 ml containing the title compound.

EXAMPLE 7
17Z- and 17E-isomers of 20,21-dihydroxypregna-1,4,9(11),17(20)-tetraen-3-one 21-acetate 20-trimethylsilyloxy ether (III)

A solution of copper propionate (0.572 g) in tetrahydrofuran (10 ml) under a nitrogen atmosphere is cooled in a dry ice/acetone bath to $-50°$. DIBAH in toluene (25% wt, 58 ml) is added to the copper solution over a 5–10 min. period keeping the temperature near $-50°$. The solution turns dark green then lightens to brown during the addition. This brown solution is allowed to stir 3.5 min., then it is added via a cannula to a 50° slurry of 21-hydroxypregna-1,4,9(11),16-tetraene-3,20-dione 21-acetate (I, U.S. Pat. No. 2,864,834 Example 1, 20.00 g) in THF (150 ml) containing dimethylimidazolidinone (9.54 ml) and N-trimethylsilylimidazone (16.0 ml) over a 25 min period. The solution is allowed to stir 10 min after complete addition, then checked by TLC, as described in EXAMPLE 6.

When the reduction is complete imidazole (1.86 g) is added and the reaction is allowed to warm to 20°–25°, after which the reaction is checked for complete silylation by TLC.

When the silylation is complete the reaction is quenched by adding it to a 0° mixture of aqueous acetic acid (1.5%, 1250 ml) and toluene (250 ml). The mixture is allowed to stir 5.10 min, then the layers are separated. The aqueous layer is extracted with toluene (2×200 ml) and the combined organic extracts are washed with water (2×300 ml) and then with saline (300 ml). The organic layer is dried over magnesium sulfate, filtered and concentrated under reduced pressure to a total volume of 220 ml containing the title compound.

EXAMPLE 8
17Z- and 17E-isomers of 20,21-dihydroxypregna-4,9(11),17(20)-trien-3-one 21-acetate 20-trimethylsilyloxy ether (III)

A solution of copper propionate (0.057 g) in THF (12 ml) under a nitrogen atmosphere is cooled in a dry ice/acetone bath to $-50°$. HMPA (1.51 ml) followed by a solution of DIBAH in toluene (25% wt, 5.44 ml) is added to the copper solution over a 5–10 min period keeping the temperature near $-50°$. The blue solution turns dark green then lightens to brown during the addition. This brown solution is allowed to stir 3.5 min, then it is added via a cannula to a −50° slurry of 21-hydroxypregna-4,9(11),16-triene-3,20-dione 21 acetate (I, U.S. Pat. No. 2,773,080 Example 1, 2.00 g) in tetrahydrofuran (25 ml) containing N-trimethylsilylimidazole (2.71 ml) over a 7 min period. The solution is allowed to stir after complete addition and checked by TLC.

When the reduction is complete, imidazole (0.185 g) is added and the reaction is allowed to warm to 20°-25°, after which the reaction is checked for complete silylation by TLC.

When the silylation is complete the reaction is quenched by adding it to a 0° mixture of aqueous acetic acid (1.5%, 210 ml) and toluene (50 ml). The mixture is allowed to stir 5.10 min, then the layers are separated. The aqueous layer is extracted with toluene (2×50 ml) and the combined organic extracts are washed with water (2×50 ml) and then with saline (50 ml). The organic layer is dried over magnesium sulfate, filtrated and concentrated under reduced pressure to give a solid which is crystallized from methanol to give the title compound.

EXAMPLE 9

17Z- and 17E-isomers of 6α-fluoro-20,21-dihydroxypregna-1,4,9(11),17(20)-tetraen-3-one 21-acetate 20-trimethylsilyl ether (III)

A blue solution of copper propionate (0.545 g) in tetrahydrofuran (110 ml) under a nitrogen atmosphere is cooled in a dry ice/acetone bath to −50°. A solution of DIBAH in toluene (25% wt, 55.27 ml) is added over a 5.10 min period keeping the temperature near −50°. The blue solution turns dark green then lightens to brown during the addition. This brown solution is allowed to stir 3-5 min, then it is added via a cannula to a slurry of 6α-fluoro-21-hydroxypregna-1,4,9(11),16-tetraene-3,20-dione 21-acetate 20(I, 20-g) in THF (150 ml) containing dimethylimidazolidinone (9.10 ml) and N-trimethylsilylimidazole (15.3 ml), precooled to −50°, over a 25 min period. The reaction mixture is permitted to stir 10 min after addition is complete and is monitored by TLC [the TLC sample is obtained by diluting 0.5 ml of the reaction mixture with tetrahydrofuran (0.5 ml) and eluting with tetrahydrofuran/heptane (40/60), title compound (III) Rf=0.64]. When the reduction is complete imidazole (1.77 g) is added and the reaction is permitted to warm to 20°-25°. After reaching 20°-25° the mixture is checked for complete silylation by TLC. When the simulation is complete the reaction is quenched by adding it to a 0° mixture of aqueous acetic acid (1,250 ml) and toluene (250 ml). The mixture is permitted to stir 5-10 min then the layers are separated. The aqueous layer is extracted with toluene (2×200 ml) and the combined organic extracts are washed with water (2×300 ml) and with saline (300 ml). The organic layer is dried over magnesium sulfate and the magnesium sulfate is removed by filtration. The toluene is removed by concentration under reduced pressure to give the title compound.

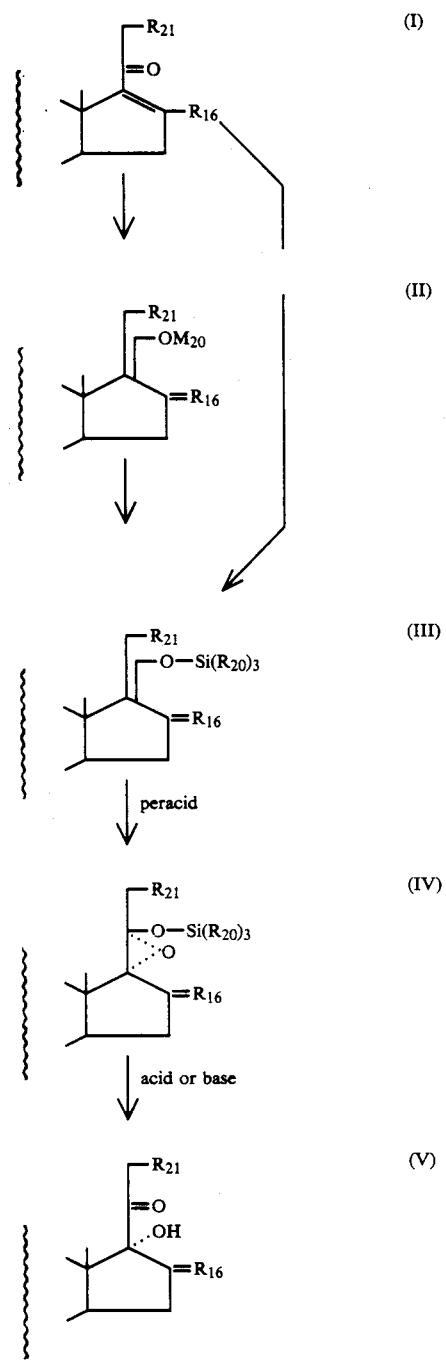

CHART A

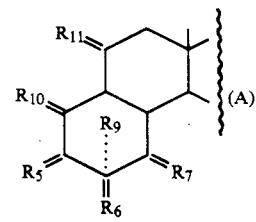

CHART B

-continued
CHART B

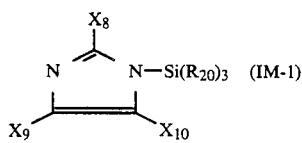 (IM-1)

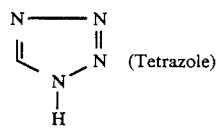 (Tetrazole)

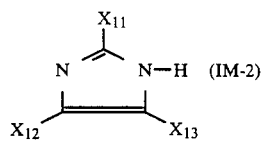 (IM-2)

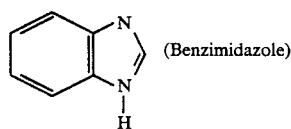 (Benzimidazole)

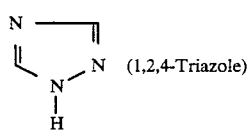 (1,2,4-Triazole)

I claim:

1. A process for the production of a metal enolate (II)

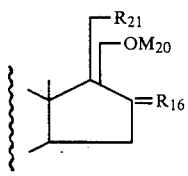 (II)

where:
$R_{16}$ is $\alpha$—H:$\beta$—$R_{16\text{-}2}$ where $R_{16\text{-}2}$ is —H or —$CH_3$;
$R_{21}$ is —H, —O—$R_{21\text{-}1}$ where $R_{21\text{-}1}$ is —H, $C_1$-$C_4$ alkyl, $CH_2$—O—$CH_3$, —$CHR_{21\text{-}2}$—O—$R_{21\text{-}3}$ where $R_{21\text{-}2}$ is $C_1$-$C_4$ alkyl and $R_{21\text{-}3}$ is $C_1$-$C_4$ alkyl. —$CH_2$—O—$CH_2CH_2$—O—$R_{21\text{-}4}$ where $R_{21\text{-}4}$ is $C_1$-$C_4$ alkyl, THP, —CO—$R_{21\text{-}5}$ where $R_{21\text{-}5}$ is $C_1$-$C_4$ or —$\phi$, —Si($R_{21\text{-}6}$)$_3$ where the $R_{21\text{-}6}$'s are the same or different and are selected from the group consisting of $C_1$-$C_4$ alkyl and —$\phi$;
$M_{20}$ is copper or a metal ion derived from the metal hydride reducing agent, which comprises contacting a $\Delta^{16}$-steroid (I)

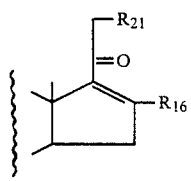 (I)

where $R_{16}$ is —H or —$CH_3$ and $R_{21}$ is as defined above with a member selected from the group consisting of a preformed copper hydride or a metal hydride reducing agent in the presence of a copper species.

2. A process for the production of a metal enolate (II) according to claim 1 where the $\Delta^{16}$-steroid (I) is of the formula

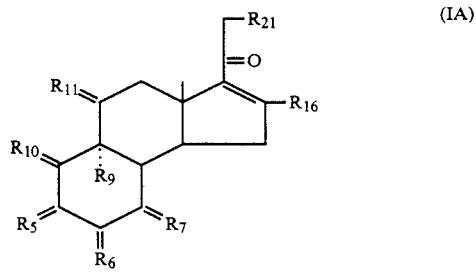 (IA)

where:
(A-I) $R_6$ is $\alpha$—$R_{6\text{-}1}$:$\beta$—$R_{6\text{-}2}$, $R_{10}$ is $\alpha$—$R_{10\text{-}1}$:$\beta$—$R_{10\text{-}2}$ and $R_7$ is $\alpha$—H:$\beta$—H where one of $R_{6\text{-}1}$ and $R_{6\text{-}2}$ is —H and the other is —H, —F or $CH_3$, $R_{10\text{-}2}$ is —$CH_3$, $R_{10\text{-}1}$ and $R_5$ taken together are —$CH_2$—$CH_2$—CO—CH= or —CH=CH—CO—CH=;

(A-II) $R_6$ is $R_{6\text{-}3}$:$R_{6\text{-}4}$, $R_7$ is $R_{7\text{-}3}$:$R_{7\text{-}4}$, $R_{10}$ is $\alpha$—$R_{10\text{-}3}$:$\beta$—$R_{10\text{-}4}$ where one of $R_{6\text{-}3}$ and $R_{6\text{-}4}$ is —H and the other taken together with one of $R_{7\text{-}3}$ and $R_{7\text{-}4}$ forms a second bond between $C_6$ and $C_7$, and the other of $R_{7\text{-}3}$ and $R_{7\text{-}4}$ is —H, $R_{10\text{-}4}$ is —$CH_3$, $R_{10\text{-}3}$ and $R_5$ taken together are —$CH_2$—$CH_2$—CO—CH= or —CH=CH—CO—CH=;

(C-I) $R_{11}$ is $R_{11\text{-}1}$:$R_{11\text{-}2}$, where one of $R_{11\text{-}1}$ and $R_{11\text{-}2}$ is taken together with $R_9$ to form a second bond between $C_9$ and $C_{11}$ and the other of $R_{11\text{-}1}$ and $R_{11\text{-}2}$ is —H;

(C-II) $R_{11}$ is $\alpha$—H:$\beta$—O— where $\beta$—O— is taken together with $R_9$ to form an epoxide between $C_9$ and $C_{11}$ in the $\beta$-configuration:

(C-III) $\alpha$—$R_9$ is —H, —Br, —Cl, —F and $R_{11}$ is =O or $\alpha$—$R_{11\text{-}3}$:$\beta$—$R_{11\text{-}4}$ where one of $R_{11\text{-}3}$ and $R_{11\text{-}4}$ is —H and the other of $R_{11\text{-}3}$ and $R_{11\text{-}4}$ is —H or —OH;

(C-IV) $R_9$ is —OH and $R_{11}$ is $\alpha$—H:$\beta$—H; $R_{16}$ is —H or —$CH_3$ and $R_{21}$ is as defined in claim 1.

3. A process for the production of a metal enolate (II) according to claim 1 where the preformed copper hydride is [($\phi_3$P)CuH]$_6$, (CuH)$_x$ where x is from 1 thru 6, LiCuH$_2$, LiCu$_2$H$_3$, Li$_2$Cu$_3$H$_5$, Li$_2$CuH$_3$, Li$_3$CuH$_4$, Li$_4$CuH$_5$, LiCuH$_6$, Li$_5$CuH$_6$, $CH_3CH_2CH_2$—C≡C—CuHLi, t-butyl-O-CuHLi and $\phi$SCuHLi.

4. A process for the production of a metal enolate (II) according to claim 1 where the metal hydride reducing agent is selected from the group consisting of (A) $(X_2)(X_3)$Al—H where $X_2$ and $X_3$ are the same or different and are $C_1$-$C_6$ alkyl;

(B) [Cation]$^+$[$(X_4)_3$Aluminum-H]$^-$ where Cation is sodium, potassium or lithium $X_4$ are the same or different and are —H or —O—$X_{4\text{-}1}$ where $X_{4\text{-}1}$ is $C_1$-$C_6$ alkyl;

(C) (Metal)$(X_5)_3$B—H where metal is sodium, potassium or lithium and $X_5$ is —H, $C_1$-$C_6$ alkyl, —O—$X_{5\text{-}1}$ where $X_{5\text{-}1}$ is $C_1$-$C_6$ alkyl, —CO—$X_{5\text{-}1}$ where $X_{5\text{-}1}$ is as defined above.

5. A process for the production of a metal enolate (II) according to claim 1 where the copper species is selected from the group consisting of
(1) Cu(I)X$_6$ where X$_6$ is —CH$_3$, —Cl, —Br, —I, —CN, acetate, propionate.,
(2) Cu(II)(X$_7$)$_n$ where X$_7$ is —CH$_3$, —Cl, —Br, —I, —CN, sulfate, acetate, propionate;
(3) dilithium tetrachlorocuprate (Li$_2$CuCl$_4$).

6. A process for the production of a metal enolate (II) according to claim 1 where the process is performed in the presence of a ligand.

7. A process for the production of a metal enolate (II) according to claim 6 where the ligand is selected from the group consisting of C$_1$-C$_8$ alkyl or —φ.

8. A process for the production of a silyl ether (III)

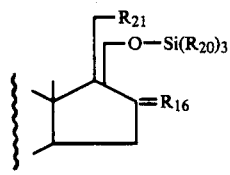

where
R$_{16}$ is α—H:β—R$_{16-2}$ where R$_{16-2}$ is —H or —CH$_3$;
R$_{20}$'s are the same or different and are C$_1$-C$_7$ alkyl or —φ;
R$_{21}$ is —H, —O—R$_{21-1}$ where R$_{21-1}$ is —H, C$_1$-C$_4$ alkyl, —CH$_{2-0}$CH$_3$, —CHR$_{21-2}$—O—R$_{21-3}$ where R$_{21-2}$ is C$_1$-C$_4$ alkyl and R$_{21-33}$ is C$_1$-C$_4$ alkyl, —CH$_2$—O—CH$_2$CH$_2$—O—R$_{21-4}$ where R$_{21-4}$ is C$_1$-C$_4$ alkyl, THP, —CO—R$_{21-5}$ where R$_{21-5}$ is C$_1$-C$_4$ or —φ, —Si(R$_{21-6}$)$_3$ where the R$_{21-6}$'s are the same or different and are selected from the group consisting of C$_1$-C$_4$ alkyl and —φ; which comprises contacting a metal enolate of formula (II)

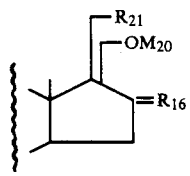

where M$_{20}$ is a copper, aluminum or boron cation, and R$_{16}$ and R$_{21}$ are as defined above, with a silylating agent.

9. A process for the production of a silyl ether (III) according to claim 8 where the silyl ether (III) is of the formula

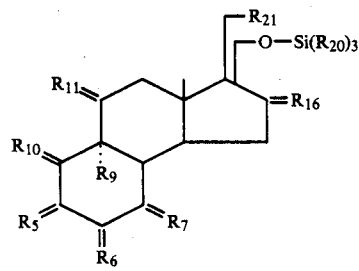

where:
(A-I) R$_6$ is α—R$_{6-1}$:β—R$_{6-2}$, R$_{10}$ is α—R$_{10-1}$:β—R$_{10-2}$ and R$_7$ is α—H:β—H where one of R$_{6-1}$ and R$_{6-2}$ is —H and the other is —H, —F or —CH$_3$, R$_{10-2}$ is —CH$_3$, R$_{10-1}$ and R$_5$ taken together are —CH$_2$—CH$_2$—CO—CH= or —CH=CH—CO—CH=;

(A-II) R$_6$ is R$_{6-3}$:R$_{6-4}$, R$_7$ is R$_{7-3}$:R$_{7-4}$, R$_{10}$ is α—R$_{10-3}$:β—R$_{10-4}$ where one of R$_{6-3}$ and R$_{6-4}$ is —H and the other taken together with one of R$_{7-3}$ and R$_{7-4}$ forms a second bond between C$_6$ and C$_7$, and the other of R$_{7-3}$ and R$_{7-4}$ is —H, R$_{10-4}$ is —CH$_3$, R$_{10-3}$ and R$_5$ taken together are —CH$_2$—CH$_2$—CO—CH= or —CH=CH—CO—CH=;

(C-I) R$_{11}$ is R$_{11-1}$:R$_{11-2}$, where one of R$_{11-1}$ and R$_{11-2}$ is taken together with R$_9$ to form a second bond between C$_9$ and C$_{11}$ and the other of R$_{11-1}$ and R$_{11-2}$ is —H;

(C-II) R$_{11}$ is α—H:β—O— where β—O— is taken together with R$_9$ to form an epoxide between C$_9$ and C$_{11}$ in the β-configuration:

(C-III) α—R$_9$ is —H, —Br, —Cl, —F and R$_{11}$ is =O or α—R$_{11-3}$: β—R$_{11-4}$ where one of R$_{11-3}$ and R$_{11-4}$ is —H and the other of R$_{11-3}$ and R$_{11-4}$ is —H or —OH;

(C-IV) R$_9$ is —OH and R$_{11}$ is α—H:β—H; and where R$_{16}$, R$_{20}$ and R$_{21}$ are as defined in claim 8.

10. A process for the production of a silyl ether (III) according to claim 8 where the silylating agent is selected from the group consisting of (1) X$_1$—Si—(R$_{20}$)$_3$ where X$_1$ is —Cl, —Br, —I and where R$_{20}$ is as defined in claim 8, in the presence of an amine catalyst; (2) a silylated imidazole of the formula

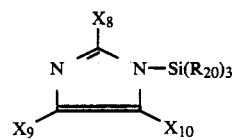

where X$_8$, X$_9$ and X$_{10}$ are the same or different and are —H or C$_1$-C$_3$ alkyl,
(3) a 1-silylated 1,2,4-triazole of the formula *NSi(R$_{20}$)$_3$—N=CX$_{17}$—N=CX$_{18}$* where X$_{17}$ and X$_{18}$ are the same or different and are —H or C$_1$-C$_3$ alkyl, and the atoms marked with an asterisk are bonded to each other resulting in the formation of a ring.
(4) a 1-silylated tetrazole of the formula N(R$_{20}$)$_3$—N=N—N—CX$_{19}$* where X$_{19}$ is —H or C$_1$-C$_3$ alkyl and where the atoms marked with an asterisk are bonded to each other resulting in the formation of a ring,
(5) a 3-silylated benzimidazole optionally substituted with 1-5 C$_1$-C$_3$ alkyl in the 2-, 4-, 5-, 6- and 7-positions.

11. A process for the production of a silyl ether (III) according to claim 10 where the amine catalyst is selected from the group consisting of pyridine triazene, tetrazene, an imidazole of the formula

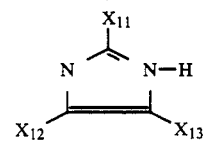

where X$_{11}$, X$_{12}$ and X$_{13}$ are the same or different and are —H or C$_1$-C$_3$ alkyl, a 1,2,4-triazole of the formula *NH—N=CX$_{14}$—N=GX$_{15}$* where X$_{14}$ and X$_{15}$ are the same or different and are —H or C$_1$-C$_3$ alkyl and the atoms marked with an asterisk are bonded to each other resulting in the formation of a ring, a tetrazole of the formula *NH—N=N—N=CX$_{16}$* where X$_{16}$ is —H or C$_1$-C$_3$ alkyl and where the atoms marked with an asterisk are bonded to each other resulting in the formation of a ring, benzimidazole optionally substituted with 1-5 C$_1$-C$_3$ alkyl in the 2-, 4-, 5-, 6- and 7-positions.

12. A process for the production of a silyl ether (III)

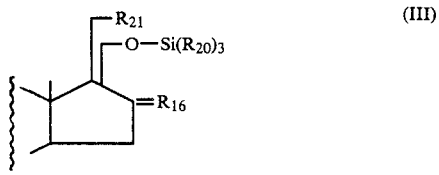

where R$_{16}$ is α—H:β—R$_{16-2}$ where R$_{16-2}$ is —H or —CH$_3$;

R$_{20}$'s are the same or different and are C$_1$-C$_7$ alkyl or —φ;

R$_{21}$ is —H, —O—R$_{21-1}$ where R$_{21-1}$ is —H, C$_1$-C$_4$ alkyl, —CH$_2$—O—CH$_3$, —CHR$_{21-2}$—O—R$_{21-3}$ where R$_{21-2}$ is C$_1$-C$_4$ alkyl and R$_{21-3}$ is C$_1$-C$_4$ alkyl, —CH$_2$—O—CH$_2$CH$_2$—O—R$_{21-4}$ where R$_{21-4}$ is C$_1$-C$_4$ alkyl, THP, —CO—R$_{21-5}$ where R$_{21-5}$ is C$_1$-C$_4$ or —φ, —Si(R$_{21-6}$)$_3$ where the R$_{21-6}$'s are the same or different and are selected from the group consisting of C$_1$-C$_4$ alkyl and —φ; which comprises contacting a $\Delta^{16}$-steroid of formula (I)

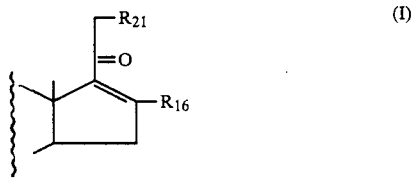

where R$_{16}$ is —H or —CH$_3$ and R$_{21}$ is as defined above with a member selected from the group consisting of a preformed copper hydride or a metal hydride reducing agent in the presence of a copper species, in the presence of a silylating agent.

13. A process for the production of a silyl ether (III) according to claim 12 where the $\Delta^{16}$-steroid (I) is of the formula

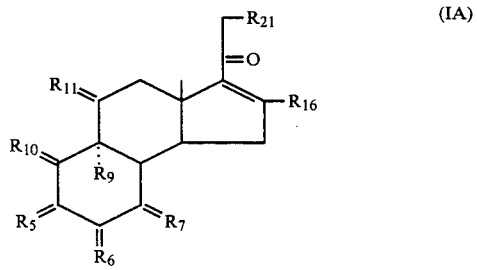

where:

(A-I) R$_6$ is α—R$_{6-1}$:β—R$_{6-2}$, R$_{10}$ is α—R$_{10-1}$:β—R$_{10-2}$ and R$_7$ is α—H where one of R$_{6-1}$ and R$_{6-2}$ is —H and the other is —H, —F or —CH$_3$, R$_{10-2}$ is —CH$_3$, R$_{10-1}$ and R$_5$ taken together are —CH$_2$—CH$_2$—CO—CH= or —CH=CH—CO—CH=;

(A-II) R$_6$ is R$_{6-3}$:R$_{6-4}$, R$_7$ is R$_{7-3}$:R$_{7-4}$, R$_{10}$ is α—R$_{10-3}$:β—$_{10-4}$ where one of R$_{6-3}$ and R$_{6-4}$ is —H and the other taken together with one of R$_{7-3}$ and R$_{7-4}$ forms a second bond between C$_6$ and C$_7$, and the other of R$_{7-3}$ and R$_{7-4}$ is —H, R$_{10-4}$ is —CH$_3$, R$_{10-3}$ and R$_5$ taken together are —CH$_2$—CH$_2$—CO—CH= or —CH=CH—CO—CH=;

(C-I) R$_{11}$ is R$_{11-1}$:R$_{11-2}$, where one of R$_{11-1}$ and R$_{11-2}$ is taken together with R$_9$ to form a second bond between C$_9$ and C$_{11}$ and the other of R$_{11-1}$ and R$_{11-2}$ is —H;

(C-II) R$_{11}$ is α—H:β—O— where β—O— is taken together with R$_9$ to form an epoxide between C$_9$ and C$_{11}$ in the β-configuration:

(C-III) α—R$_9$ is —H, —Br, —Cl, —F and R$_{11}$ is =O or α—R$_{11-3}$:β—R$_{11-4}$ where one of R$_{11-3}$ and R$_{11-4}$ is —H and the other of R$_{11-3}$ and R$_{11-4}$ is —H or —OH;

(C-IV) R$_9$ is —OH and R$_{11}$ is α—H:β—H; and where R$_{16}$ and R$_{21}$ are as defined in claim 12.

14. A process for the production of a silyl ether (III) according to claim 12 where the preformed copper hydride is [(φ$_3$P)CuH]$_6$, (CuH)$_x$ where x is from 1 thru 6, LiCuH$_2$, LiCu$_2$H$_3$, Li$_2$Cu$_3$H$_5$, Li$_2$CuH$_3$, Li$_3$CuH$_4$, Li$_4$CuH$_5$, LiCuH$_6$, Li$_5$CuH$_6$, CH$_3$CH$_2$CH$_2$—C≡C—CuHLi, t-butyl—O— CuHLi and φSCuHLi.

15. A process for the production of a silyl ether (III) according to claim 12 where the metal hydride reducing agent is selected from the group consisting of (A) (X$_2$)(X$_3$)Al—H where X$_2$ and X$_3$ are the same or different and are C$_1$-C$_6$ alkyl;

(B) [Cation]$^+$[(X$_4$)$_3$Aluminum-H]$^-$ where Cation is sodium, potassium or lithium X$_4$ are the same or different and are —H or —O—X$_{4-1}$ where X$_{4-1}$ is C$_1$-C$_6$ alkyl;

(C) (Metal)(X$_5$)$_3$B—H where metal is sodium potassium or lithium and X$_5$ is —H, C$_1$-C$_6$ alkyl.

—O—X$_{5-1}$ where X$_{5-1}$ is C$_1$-C$_6$ alkyl,

—CO—X$_{5-1}$ where X$_{5-1}$ is as defined above.

16. A process for the production of a silyl ether (III) according to claim 12 where the copper species is selected from the group consisting of (1) Cu(I)X$_6$ where X$_6$ is —CH$_3$, —Cl, —Br, —I, —CN, acetate, propionate;

(2) Cu(II)(X$_7$)$_n$ where X$_7$ is —CH$_3$, —Cl, —Br, —I, —CN, sulfate, acetate, propionate., (3) dilithium tetrachlorocuprate (Li$_2$CuCl$_4$).

17. A process for the production of a silyl ether (III) according to claim 12 where the process is performed in the presence of a ligand.

18. A process for the production of a silyl ether (III) according to claim 17 where the ligand is selected from the group consisting of HMPA, DMI, DMPU, TMU, NMP, TES, DMAP, TMEDA and (X$_{20}$)$_3$P where X$_{20}$ is C$_1$-C$_8$ alkyl or —φ.

19. A process for the production of a silyl ether (III) according to claim 12 where the silylating agent is selected from the group consisting of (1) X$_1$—Si—(R$_{20}$)$_3$ where X$_1$ is —Cl, —Br, —I and where R$_{20}$ is as defined in claim 12 in the presence of an amine catalyst; (2) a silylated imidazole of the formula

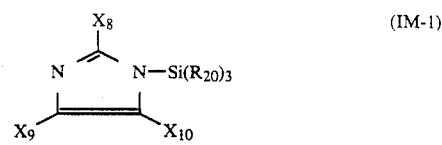

where $X_8$, $X_9$ and $X_{10}$ are the same or different and are —H or $C_1$–$C_3$ alkyl, (3) a 1-silylated 1,2,4-triazole of the formula *NSi$(R_{20})_3$—N=C$X_{17}$—N=C$X_{18}$* where $X_{17}$ and $X_{18}$ are the same or different and are —H or $C_1$–$C_3$ alkyl, and the atoms marked with an asterisk are bonded to each other resulting in the formation of a ring, (4) a 1-silylated tetrazole of the formula *N$(R_{20})_3$—N=N—N=C$X_{19}$* where $X_{19}$ is —H or $C_1$–$C_3$ alkyl and where the atoms marked with an asterisk are bonded to each other resulting in the formation of a ring;

(5) a 3-silylated benzimidazole optionally substituted with 1–5 $C_1$–$C_3$ alkyl in the 2-, 4-, 5-, 6- and 7-positions.

20. A process for the production of a silyl ether (III) according to claim 12 where the amine catalyst is selected from the group consisting of pyridine, triazene tetrazene, an imidazole of the formula

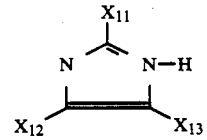
(IM-2)

where $X_{11}$, $X_{12}$ and $X_{13}$ are the same or different and are —H or $C_1$–$C_3$ alkyl, a 1,2,4-triazole of the formula *NH—N=C$X_{14}$—N=C$X_{15}$* where $X_{14}$ and $X_{15}$ are the same or different and are —H or $C_1$–$C_3$ alkyl and the atoms marked with an asterisk are bonded to each other resulting in the formation of a ring, a tetrazole of the formula *NH—N=N—N=C$X_{16}$* where $X_{16}$ is —H or $C_1$–$C_3$ alkyl and where the atoms marked with an asterisk are bonded to each other resulting in the formation of a ring, benzimidazole optionally substituted with 1–5 $C_1$–$C_3$ alkyl in the 2-, 4-, 5-, 6- and 7-positions.

21. A process for the production of a silyl ether (III) according to claim 15 which is a mixture of the 17Z- and 17E-isomers of 6α-fluoro-20,21-dihydroxypregna-1,4,9(11),17(20)-tetrazene-3-one 21-acetate 20-trimethylsilyl ether, 20,21-dihydroxy-16β-methylpregna-1,4,9(11),17(20)-tetraen-3-one 21-acetate 20-trimethylsilyl ether, 9β,11β-epoxy-20,21-dihydroxypregna-1,4,17(20)-trien-3-one 21-acetate 20-trimethylsilyloxy ether, 20,21-dihydroxypregna-1,4,9(11),17(20)-tretraen-3-one 21-acetate 20-trimethylsilyloxy ether, 20,21-dihydroxypregna-4,9(11),17(20)-trien-3-one 21-acetate 20-trimethylsilyloxy ether.

* * * * *

UNITED STATES PATENT AND TRADEMARK OFFICE
CERTIFICATE OF CORRECTION

PATENT NO. : 4,975,536

DATED : December 4, 1990

INVENTOR(S) : Kenneth P. Shephard

It is certified that error appears in the above-identified patent and that said Letters Patent is hereby corrected as shown below:

On the title page before item [57] insert --Attorney, Agent, or Firm - Bruce Stein--.

Signed and Sealed this

Seventh Day of April, 1992

Attest:

HARRY F. MANBECK, JR.

Attesting Officer

Commissioner of Patents and Trademarks